(12) United States Patent
Mueller

(10) Patent No.: US 9,642,672 B2
(45) Date of Patent: *May 9, 2017

(54) FERROFLUIDIC LOCK

(71) Applicant: COVIDIEN LP, Mansfield, MA (US)

(72) Inventor: Peter Michael Mueller, Frederick, CO (US)

(73) Assignee: COVIDIEN LP, Mansfield, MA (US)

( * ) Notice: Subject to any disclaimer, the term of this patent is extended or adjusted under 35 U.S.C. 154(b) by 350 days.

This patent is subject to a terminal disclaimer.

(21) Appl. No.: 14/552,564

(22) Filed: Nov. 25, 2014

(65) Prior Publication Data

US 2015/0080888 A1    Mar. 19, 2015

Related U.S. Application Data

(63) Continuation of application No. 12/986,766, filed on Jan. 7, 2011, now Pat. No. 8,906,019.

(51) Int. Cl.
*A61B 18/18* (2006.01)
*A61B 18/14* (2006.01)
(Continued)

(52) U.S. Cl.
CPC .......... *A61B 18/1445* (2013.01); *A61B 17/29* (2013.01); *A61B 2017/00318* (2013.01);
(Continued)

(58) Field of Classification Search
CPC ..... A61B 18/08; A61B 18/082; A61B 18/085; A61B 18/14; A61B 18/1402; A61B 18/1442; A61B 18/1445; A61B 18/144; A61B 2018/1442; A61B 2018/145; A61B 2018/1452; A61B 2018/1455; A61B 2018/1457; A61B 2018/146; A61B 2018/1462; A61B 2017/2946
See application file for complete search history.

(56) References Cited

U.S. PATENT DOCUMENTS 4,890,602 A  *  1/1990  Hake .................... A61B 1/0053
                                              600/144
4,971,033 A  * 11/1990  Ehlers .................. A61B 1/0056
                                              600/139
(Continued)

*Primary Examiner* — Joseph Stoklosa
*Assistant Examiner* — Eunhwa Kim

(57) ABSTRACT

A surgical instrument includes a housing and an elongated shaft extending distally therefrom. The elongated shaft includes a proximal portion, a distal portion and a flexible portion supported therebetween. The flexible portion permits pivotal movement of the distal portion of the elongated shaft and an end effector supported thereon. A locking mechanism is operatively associated with the flexible portion of the elongated shaft to selectively impede pivotal motion of the distal portion. The locking mechanism includes a fluid chamber defined within the flexible portion in which a variable viscosity fluid disposed. The variable viscosity fluid is responsive to the application of an electromagnetic field to exhibit increased rigidity in the presence of the electromagnetic field and reduced rigidity in the absence of the electromagnetic field. An electrical coil is arranged such that the electromagnetic field may be selectively induced by the delivery of electrical energy from a power source.

18 Claims, 5 Drawing Sheets

(51) Int. Cl.
*A61B 17/29* (2006.01)
*A61B 17/00* (2006.01)

(52) U.S. Cl.
CPC ............... *A61B 2017/00398* (2013.01); *A61B 2017/2946* (2013.01)

(56) References Cited

U.S. PATENT DOCUMENTS

| | | |
|---|---|---|
| 5,374,277 A | 12/1994 | Hassler |
| 5,601,572 A | 2/1997 | Middleman et al. |
| 5,673,840 A | 10/1997 | Schulze et al. |
| 7,588,546 B2 | 9/2009 | de Andrade |
| 7,615,067 B2 | 11/2009 | Lee et al. |
| 8,906,019 B2 | 12/2014 | Mueller |
| 2006/0258978 A1 | 11/2006 | Vanney |
| 2006/0258979 A1* | 11/2006 | Fischer ............. A61M 25/0136 604/95.04 |
| 2007/0027468 A1 | 2/2007 | Wales et al. |
| 2007/0219550 A1 | 9/2007 | Thompson et al. |
| 2009/0137984 A1* | 5/2009 | Minnelli ............ A61B 17/0218 604/540 |
| 2010/0324370 A1* | 12/2010 | Dohi ................. A61B 1/00078 600/144 |

\* cited by examiner

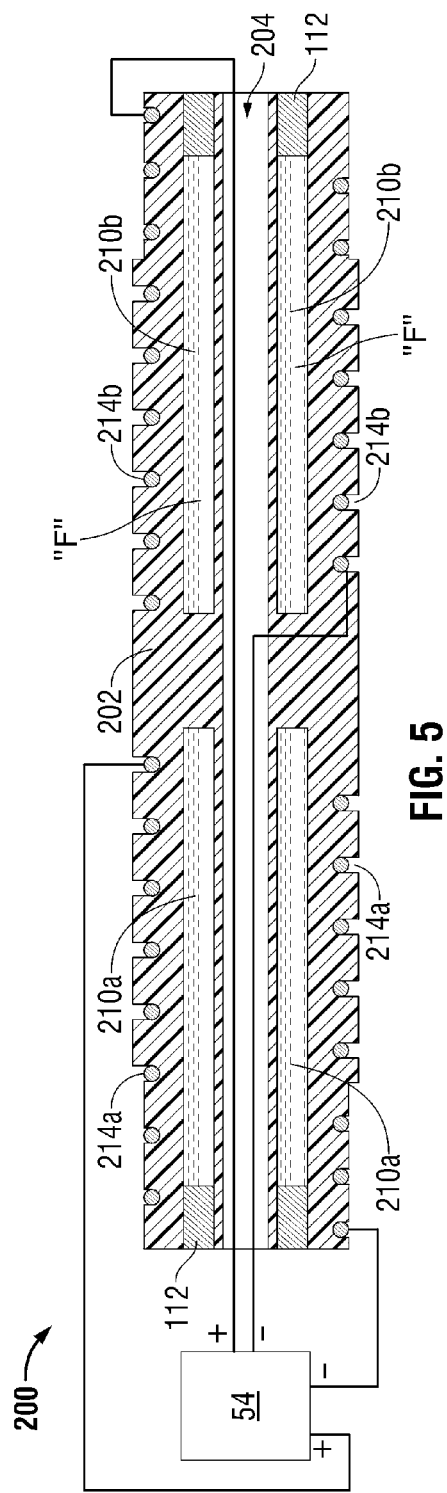
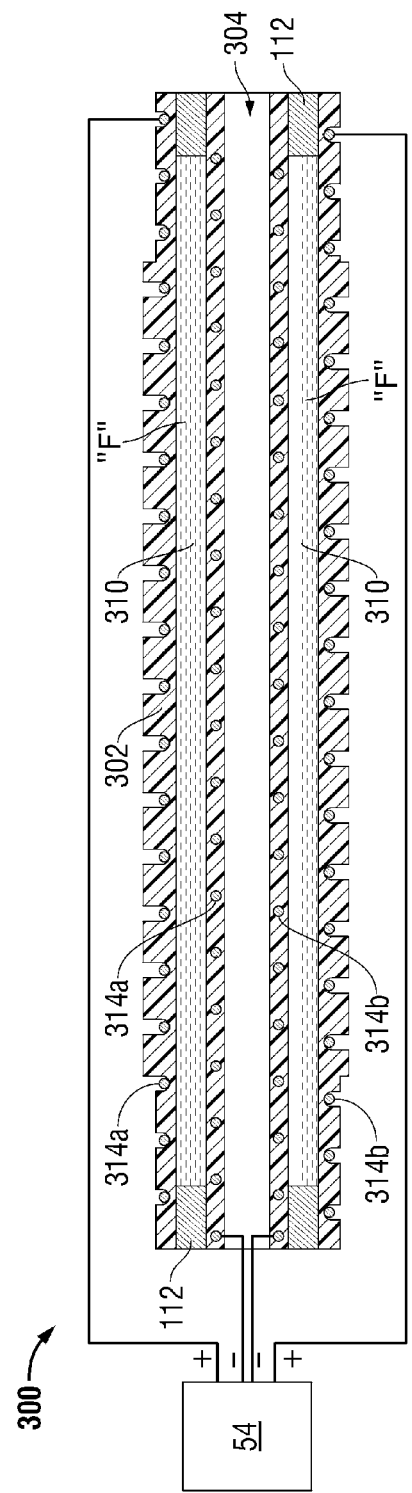

FERROFLUIDIC LOCK

CROSS-REFERENCE TO RELATED APPLICATIONS

This application is a continuation application of U.S. patent application Ser. No. 12/986,766, filed on Jan. 7, 2011, the entire contents of which are hereby incorporated herein by reference.

BACKGROUND

1. Technical Field

The present disclosure relates to a surgical apparatus for laparoscopic and endoscopic procedures. In particular, the disclosure relates to a surgical apparatus having a locking mechanism for maintaining a remotely-actuated component of the instrument at a particular position or orientation.

2. Background of Related Art

Typically in a laparoscopic, endoscopic, or other minimally invasive surgical procedure, a small incision or puncture is made in a patient's body. A cannula is then inserted into a body cavity through the incision, which provides a passageway for inserting various surgical devices such as scissors, dissectors, retractors, or similar instruments. To facilitate operability through the cannula, instruments adapted for laparoscopic or endoscopic surgery typically include a relatively narrow, elongated shaft extending distally from a housing, and supporting an end effector at its distal end. Arranging the shaft of such an instrument through the cannula allows a surgeon to manipulate actuators on the housing from outside the body to induce the end effector to carry out a surgical procedure at a remote internal surgical site. This type of minimally invasive procedure has proven beneficial over traditional open surgery due to reduced trauma, improved healing and other attendant advantages.

Some laparoscopic or endoscopic instruments are steerable, and thus may provide a surgeon with a range of operability suitable for a particular surgical purpose. For example, an instrument may be configured such that the end effector may be aligned with a longitudinal axis of the instrument to facilitate insertion of the elongated shaft through the cannula. Thereafter, the end effector may be induced to articulate, or move off-axis as necessary to appropriately orient the end effector for engaging the targeted tissue. Some mechanisms for articulating the distal end of an endoscopic instrument include a pair of tendons, or tension-bearing drive cables, with distal ends anchored to the articulating portion of the instrument on opposite sides of the longitudinal axis. The proximal ends of the drive cables are operatively coupled to an actuator on the housing that is responsive to manipulation by the surgeon to draw one of the drive cables proximally while simultaneously permitting distal motion in the other drive cable. This motion in the drive cables induces pivotal motion of the articulating portion of the instrument.

When the end effector of a steerable, articulating instrument has been satisfactorily positioned and oriented, a surgeon may maintain the position and orientation of the end effector by continuously exerting the necessary forces on the actuators at the housing. Alternatively, some instruments are provided with a locking mechanism that permits the surgeon to temporarily lock the position and orientation of the end effector so that a continuous exertion of force at the housing is not required. Often these locking mechanisms operate by engaging the drive cables within the housing to arrest their motion. However, regardless of the construction materials, the drive cables exhibit a spring rate that is amplified over the length of the drive cables, and thus, the drive cables may tend to stretch when external loads are applied to the elongated shaft. This tendency to stretch may be associated with an unintended change in orientation of the end effector, e.g., without a corresponding manipulation of the actuators initiated by the surgeon.

SUMMARY

The present disclosure describes a surgical instrument including a housing and an elongated shaft extending distally from the housing, the elongated shaft includes a proximal portion defining a longitudinal axis, a distal portion, and at least one flexible portion supported between the proximal and distal portions to permit pivotal movement of the distal portion of the elongated shaft with respect to the longitudinal axis. An end effector is supported by the distal portion of the elongated shaft, and is adapted for surgically treating tissue. A locking mechanism is operatively associated with the at least one flexible portion of the elongated shaft to selectively impede pivotal motion of the distal portion of the elongated shaft. The locking mechanism includes a fluid chamber defined within the flexible portion of the elongated shaft and a variable viscosity fluid disposed within the fluid chamber. The variable viscosity fluid is responsive to the application of an electromagnetic field such that the variable viscosity fluid exhibits an increased rigidity in the presence of the electromagnetic field and a reduced rigidity in the absence of the electromagnetic field. An electrical coil is coupled to a power source and extends at least partially through the flexible portion of the elongated shaft. The electrical coil is arranged such that the electromagnetic field may be selectively induced by the delivery of electrical energy from the power source to the coil.

The variable viscosity fluid may include a ferrofluid. The power source may be operatively associated with a locking actuator supported by the housing, and the locking actuator may be operable between a locked position wherein the power source supplies electrical energy to the coil and an unlocked position wherein the power source prohibits the delivery of electrical energy to the coil. The locking actuator may also be responsive to movement to intermediate positions between the locked and unlocked positions to progressively increase and decrease the delivery of electrical energy to the coil.

A plurality of radially spaced fluid chambers may be defined within the flexible portion of the elongated shaft, and the coil may encircle each of the plurality of radially spaced fluid chambers. Alternatively or additionally, a plurality of longitudinally spaced fluid chambers may be defined in the flexible portion of the elongated shaft, and wherein a plurality of correspondingly longitudinally spaced coils may be arranged in the flexible portion of the elongated shaft. Each of the plurality of longitudinally spaced coils may be independently coupled to the power source such that an independent supply of electrical energy may be delivered to each of the longitudinally spaced coils.

The surgical instrument may also include at least one articulation cable extending at least partially through the elongated shaft. A distal end of the articulation cable may be operatively coupled to the distal portion of the elongated shaft and a proximal end of the articulation cable may be operatively coupled an articulation actuator such that manipulation of the articulation actuator induces an attendant pivotal motion of the distal portion of the elongated shaft with respect to the longitudinal axis.

The end effector may include a pair of jaw members, and at least one of the jaw members may be selectively movable between an open position substantially spaced from the other of the pair of jaw members and a closed position wherein the jaw members are closer together. At least one of the pair of jaw members may be adapted to couple to a source of electrosurgical energy that is independent from the electrical energy delivered to the coil.

According to another aspect of the disclosure, an articulating surgical instrument includes a housing and an elongated shaft extending distally from the housing. The elongated shaft includes a proximal portion defining a longitudinal axis, a distal portion pivotally coupled to the proximal portion, and at least one flexible portion supported between the proximal and distal portions of the elongated shaft. An end effector is supported by the distal portion of the elongated shaft, and the end effector is adapted for surgically treating tissue. At least one tensile member extends longitudinally through the elongated shaft. The at least one tensile member is selectively movable to induce an attendant bending of the flexible portion of the elongated shaft and a corresponding pivotal motion of the distal portion of the elongated shaft. A locking mechanism is operatively associated with the flexible portion of the elongated shaft to selectively vary the rigidity of the flexible portion of the elongated shaft. The locking mechanism includes a variable viscosity fluid disposed within the flexible portion of the elongated shaft. The variable viscosity fluid is responsive to an electromagnetic field such that the variable viscosity fluid exhibits an increased rigidity in the presence of the electromagnetic field and a reduced rigidity in the absence of the electromagnetic field. The locking mechanism also includes a field generator selectively operable to apply and remove the electromagnetic field.

The at least one tensile member may include at least one pair of articulation cables selectively movable in opposed longitudinal directions to induce the attendant pivotal motion of the distal portion of the elongated shaft. The flexible portion of the elongated shaft may include an elongated extrusion constructed of a flexible material, and the at least one pair of articulation cables may be slidably disposed within at least one pair of articulation lumens extending through the elongated extrusion.

The variable viscosity fluid may be disposed within at least one fluid chamber defined in the elongated extrusion. The field generator may include a coiled conductor arranged about the at least one fluid chamber, and the coiled conductor may be electrically coupled to a power source disposed within the housing. The coiled conductor may be arranged in a relief notch defined in an exterior surface of the elongated extrusion that extends longitudinally along the elongated extrusion. A central lumen may be defined through the elongated extrusion, and wherein a return conductor may extend through the central lumen to couple a distal end of the coiled conductor to the power source.

The elongated extrusion may also include a pair of end sections that exhibit a reduced diameter with respect to a longitudinally central portion of the elongated extrusion. The end sections may be dimensioned to engage the proximal and distal portions of the elongated shaft.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

FIG. 5 is a cross-sectional, schematic view of an alternate embodiment of an articulating portion of an instrument depicting a plurality of longitudinally spaced locking mechanisms; and FIG. 6 is a cross-sectional, schematic view of another alternate embodiment of an articulating portion of an instrument, depicting a plurality of radially-spaced locking mechanisms.

DETAILED DESCRIPTION

Figure 1:
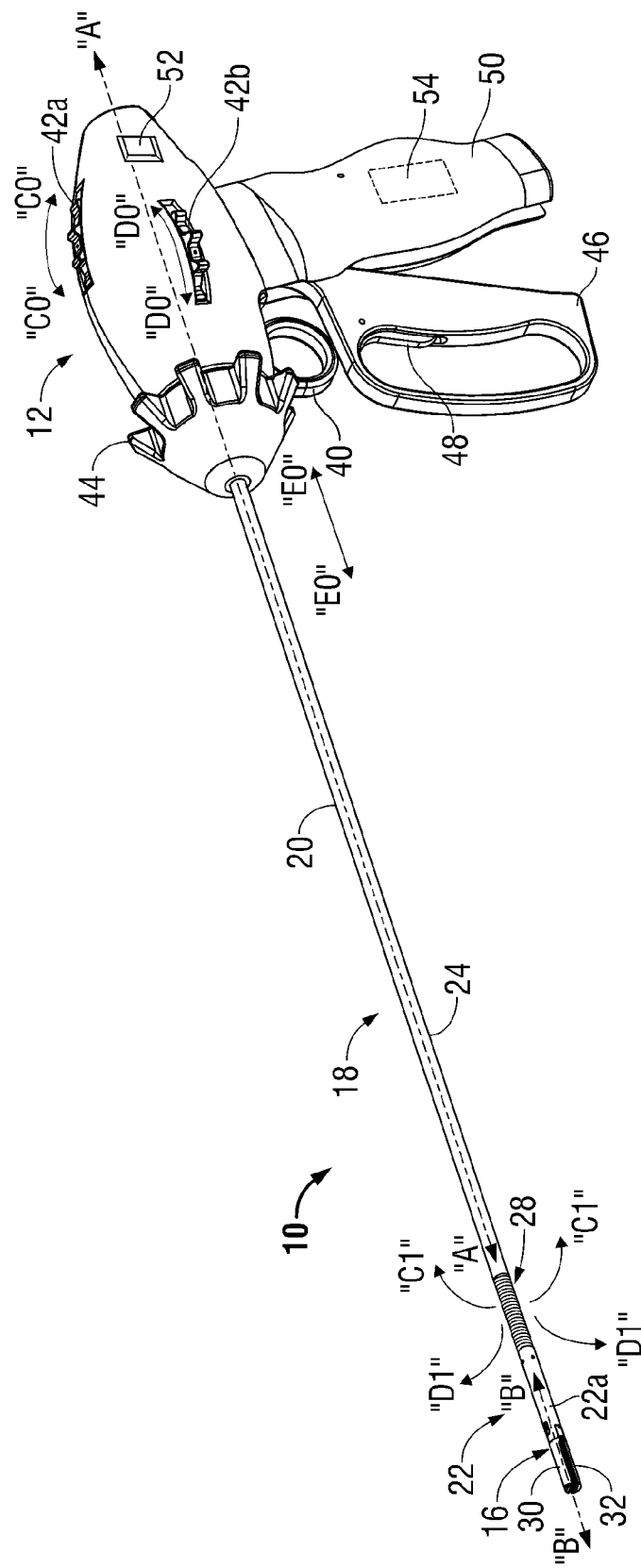
FIG. 1 is a perspective view of a surgical instrument in accordance with an embodiment of the present disclosure depicting an end effector in an aligned orientation with respect to a longitudinal axis.

Referring initially to FIG. 1, a steerable endoscopic instrument 10 is depicted generally as instrument 10. Instrument 10 includes a housing 12 near a proximal end, an end effector 16 near a distal end and an elongated shaft 18 therebetween. Elongated shaft 18 includes a proximal portion 20 extending distally from the housing 12 and an articulating distal portion 22 supporting the end effector 16. The articulating distal portion 22 includes an outer end effector support tube 22a. The proximal portion 20 defines a longitudinal axis A-A, and is sufficiently long to position the end effector 16 through a cannula (not shown) at an operative site. An outer tubular member 24 is provided over the proximal portion 20, and together with the end effector support tube 22a, provides protection and support to the interior mechanisms therein (see, e.g., FIG. 2). At least one joint or flexible portion 28 is established between the proximal and distal portions 20, 22 of the elongated shaft 18 permitting the distal portion 22 and the end effector 16 to articulate or pivot relative to the longitudinal axis A-A as described in greater detail below (see, e.g., FIG. 4). The end effector 16 defines an end effector axis B-B, which is aligned with the longitudinal axis A-A when the articulating distal portion 22 of the elongated shaft 18 is in a "home" configuration.

The end effector 16 includes a pair of opposing jaw members 30 and 32. The jaw members 30, 32 are operable from the housing 12 to move between a closed configuration and an open configuration (see FIG. 4). When the end effector 16 is in the closed configuration, a distal portion of each of the jaw members 30, 32 is adjacent the distal portion of the other of the jaw members 30, 32. The closed configuration allows the end effector 16 to assume a narrow profile to facilitate insertion of the end effector 16 through the cannula (not shown) into a body cavity. Inside the body cavity, the jaw members 30, 32 may be moved to the open configuration in which the distal portions of the jaw members 30, 32 are substantially spaced to receive tissue therebetween. The end effector 16 is configured for unilateral movement wherein only movable jaw member 32 moves relative to the end effector axis B-B (while stationary jaw member 30 remains stationary relative to the end effector axis B-B) as the end effector 16 is moved between the open and closed configurations. However, bilateral motion is also contemplated wherein both of the jaw members 30, 32 are configured to be moveable relative to the axis B-B.

Housing 12 is accessible by the surgeon from outside the body cavity to control the positioning, orientation and operation of the end effector 16 when the end effector 16 is positioned inside the body cavity at a surgical site. To provide this operability, the housing 12 supports various actuators that are operable to induce or prohibit movement in the end effector 16 through various modes. These actuators include a locking trigger 40, and a pair of articulation dials 42a, 42b. The articulation dials 42a, 42b are operable to pivot the distal portion 22 of the elongated shaft 18 to various articulated orientations with respect to the longitudinal axis A-A. For example, articulation dial 42a may be rotated in the direction of arrows "C0" to induce pivotal movement in a first plane, e.g., a vertical plane, as indicated by arrows "C1." Similarly, articulation dial 42b may be rotated in the direction of arrows "D0" to induce pivotal movement in a second plane, e.g., a horizontal plane, as indicated by arrows "D1."

The trigger 40 is operatively associated with a locking mechanism 100 to selectively adjust the rigidity of the flexible portion 28 as described below with reference to FIG. 3. The locking trigger 40 is movable in a longitudinal direction as indicated by arrows "E0" between locked and unlocked positions. When the trigger 40 is in the unlocked position, e.g., a proximal position, the flexible portion 28 is pliable, and the articulation dials 42a, 42b are functional as described above. However, when the trigger 40 is in the locked position, e.g., a distal position, the flexible portion is substantially more rigid, and the articulation dials 42a, 42b are inoperable to pivot the distal portion 22 of the elongated shaft 18 as described in greater detail below. Thus, the trigger 40 is operable to lock and maintain the end effector 16 in a particular orientation with respect to the longitudinal axis A-A. As described in greater detail below, the trigger 40 may also be movable to intermediate positions to incrementally or progressively increase and decrease resistance to articulating motion as the locking trigger 40 is moved toward the locked position.

Other actuators include shoulder roll knob 44, a pivoting handle 46 and a finger trigger 48. The shoulder roll knob 44 is operable to rotate the elongated shaft 18 about the longitudinal axis A-A, and may thus cooperate with the articulation dials 42a, 42b to permit the end effector 16 to be appropriately positioned and oriented in a three dimensional environment to effectively engage tissue. The pivoting handle 46 may be approximated and separated relative to a stationary handle 50 to move the jaw members 30, 32 between the open and closed configurations. Finger trigger 48 is operable to lock the pivoting handle 46 in an approximated position with respect to the stationary handle 50, and thus maintain the jaw members 30, 32 in the closed configuration.

When the jaw members 30, 32 are in the closed configuration, the surgeon may initiate the delivery of electrosurgical energy to the jaw members 30, 32 by manipulating a push button 52 provided on the housing 12. In alternate embodiments, the delivery of electrosurgical energy may be initiated with a footswitch (not shown) or other external actuators. Push button 52 is in electrical communication with a source of electrosurgical energy such as electrosurgical generator 54. The electrosurgical generator 54 serves to produce electrosurgical energy and also to control and monitor the delivery of the electrosurgical energy. Various types of electrosurgical generators 54, such as those generators provided by Covidien—Energy-based Devices, of Boulder, Colo., may be suitable for this purpose. Electrosurgical generator 54 may be housed within the stationary handle 50 as depicted schematically in FIG. 1, or may alternatively be electrically and mechanically coupled to the instrument 10 by a cable (not shown). The electrosurgical generator 54 is in electrical communication with at least one of the jaw members 30, 32.

Figure 2:
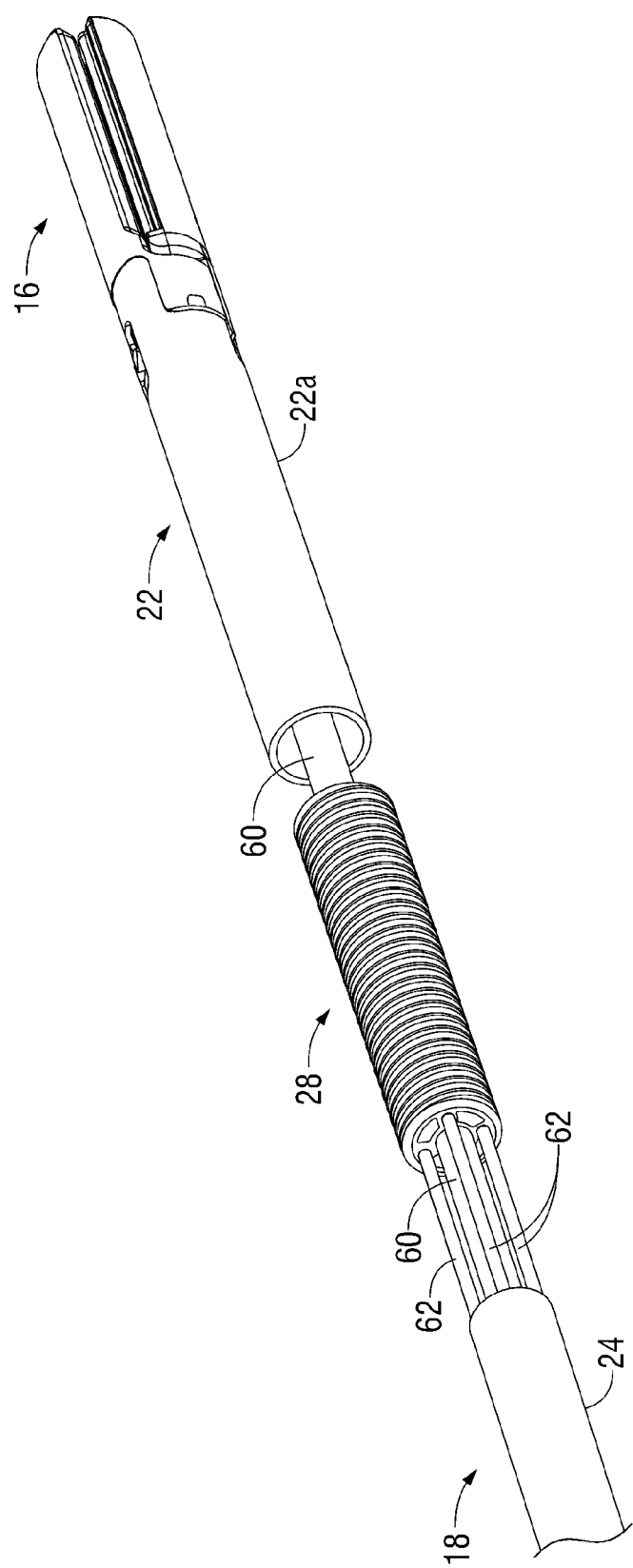
FIG. 2 is a partially exploded, perspective view of a distal end of the instrument depicting a set of drive cables extending to an articulating portion of the instrument that is arranged in a straight configuration for maintaining the end effector in the aligned orientation.

Referring now to FIG. 2 the elongated shaft 18 is depicted with the end effector support tube 22a and the outer tubular member 24 separated from the flexible portion 28. The flexible portion 28 includes a pliable material to permit elastic bending of the flexible portion 28. In other embodiments (not shown) the flexible portion 28 may be constructed of a plurality of discrete rigid segments that are pivotally arranged with respect to one another to permit the distal portion 22 to pivot relative to the longitudinal axis A-A (FIG. 1). The flexible portion 28 permits passage of a drive tube 60 therethrough. The drive tube 60 is operatively associated with the pivoting handle 46 and the end effector 16 such that manipulation of the pivoting handle 46 induces movement of the jaw members 30, 32 between the open and closed configurations. The drive tube 60 may be configured to transmit tensile, compressive or torsion loads to the jaw members, or alternatively, the drive tube 60 may house additional drive members (not shown) for moving the jaw members 30, 32.

The flexible portion 28 also permits passage of four tensile members, such as articulation cables 62. A distal end of each of the articulation cables 62 is secured to a distalmost portion of the flexible portion 28, or may alternatively be secured to a component of distal articulating portion 22 such as the end effector support tube 22a. A proximal end (not shown) of each articulation cable 62 is operatively associated with one of the articulation dials 42a, 42b (FIG. 1). The articulation dials 42a, 42b each impart opposed longitudinal motion (see FIG. 4) to the articulation cables 62, and thus pivotal motion of the distal portion 22 about the flexible portion 28. The articulation cables 62 are arranged near an outer circumference of the flexible portion 28 and have a radial spacing of about 90 degrees. Thus, the articulation cables 62 define two orthogonal planes of articulation in which the distal portion 22 may pivot.

The articulation cables 62 may be constructed of stainless steel wire or other material suitable for transmitting tensile forces to the distal-most segment 60a. Regardless of the construction materials, the articulation cables 62 exhibit a spring rate that is amplified over the length of the articulation cables 62, and thus, the articulation cables 62 may tend to stretch when external loads are applied to the elongated shaft 18. This tendency to stretch may be associated with an unintended change in orientation of the distal portion 22 of the elongated shaft 18, e.g., without a corresponding movement of the articulation dials 42a, 42b initiated by the surgeon. To diminish this unintended movement of the articulation cables 62 and end effector 16, a locking mechanism 100 (FIG. 3) that permits the flexible portion 28 to exhibit a variable rigidity without directly engaging the articulation cables 62.

Figure 3:
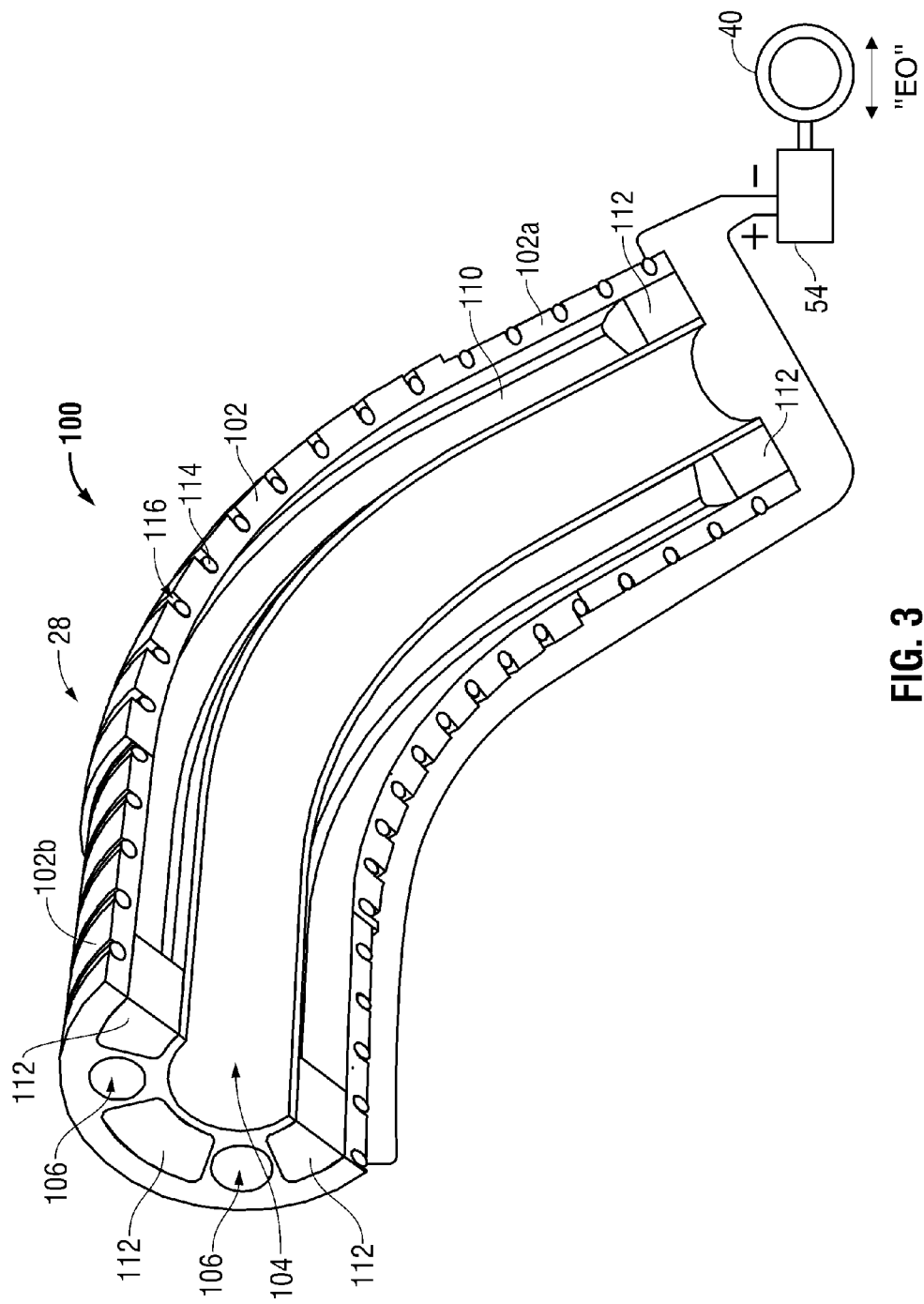
FIG. 3 is a cross-sectional, perspective view of the articulating portion of the instrument arranged in a curved configuration, depicting a locking mechanism configured for selectively maintaining the configuration of the articulating portion of the instrument, and thus the orientation of the end effector.

Referring now to FIG. 3, the locking mechanism 100 is depicted with the flexible portion 28 in a curved configuration. The flexible portion 28 includes an elongated extrusion 102 constructed of a flexible, medical-grade material. Plastic and/or elastomeric materials that are sufficiently flexible, dimensionally stable, electrically insulating, and non-irritating when placed in contact with skin and other tissues may be included in the construction of the elongated extrusion 68. The extrusion 102 includes end sections 102a and 102b that exhibit a reduced diameter to facilitate coupling the flexible portion 28 between the end effector support tube 22a and the outer tubular member 24 (FIG. 2). A central lumen 104 is defined in the elongated extrusion 102 and is dimensioned to permits passage of the drive tube 60 (FIG. 2) therethrough. Spaced radially around the central lumen 104, a set of articulation lumens 106 are defined in the extrusion 102 to permit passage and sliding movement of the articulation cables 62 (FIG. 2).

To provide the flexible portion 28 with a variable rigidity, a variable viscosity material such as a ferrofluid "F" is included in a plurality of fluid chambers 110 defined in the extrusion 102. Plugs 112 are provided at the longitudinal extremities of the fluid chambers 110 to maintain the ferrofluids "F" therein. Typically, ferrofluids include magnetic particles, such as magnetite, dispersed and suspended in a carrier fluid, and thus, the ferrofluids tend to exhibit a change in viscosity in response to an applied electromagnetic field. In the presence of an electromagnetic field, the magnetic particles are induced to line up and rigidize the extrusion 102 to a degree that is proportional to the magnitude or strength of the electromagnetic field. To facilitate the generation of an electromagnetic field, a coiled wire 114 is arranged around the fluid chambers 110 in a relief notch or spiral groove 116 defined in an exterior surface of the extrusion 102. Inducing an electric current to flow through the coiled wire 114 generates an electromagnetic field around the fluid chambers 110. The electromagnetic field may have poles oriented along an axis of the extrusion 102 such that the ferrofluids tend to rigidize the extrusion 102 with whatever curvature was imparted to the extrusion 102 when the electromagnetic field was generated.

The coiled wire 114 is coupled to a power source provided as part of the electrosurgical generator 54. The power source may be a separate component of the generator 54 such that the current provided to the coiled wire 114 is independent of the electrosurgical current that is provided to the jaw members 30, 32 (FIG. 1). Alternatively, the power source may be provided as a separate module entirely independent of the generator 54. A proximal end of the coiled wire 114 is coupled to a negative (−) terminal of the generator 54, and the distal end of the coiled wire 114 is coupled to a positive (+) or return terminal. The distal end of the coiled wire 114 may return to the generator 54 through the central lumen 104, an additional longitudinal lumen (not shown) provided in the extrusion 102, or may alternatively return in a spiral path through a spiral notch (not shown).

The generator 54 is operatively coupled to the locking trigger 40 to control the supply of an electrical current to the coiled wire 114. The flow of an electric current through the coiled wire 114 generates an electromagnetic field about the fluid chambers 110, and the electromagnetic field, in turn, increases the viscosity of the ferrofluid "F" within the fluid chambers 110. The characteristics of the electrical current supplied, and thus the characteristics of the electromagnetic field generated, and the resultant viscosity of the ferrofluid "F" may be dependent on the degree that the locking trigger 40 is moved toward a locked position. For example, the magnitude of the electromagnetic field generated may be proportional to the distance the locking trigger 40 is moved in the direction of the arrows "E0." The degree to which the ferrofluids "F" in fluid chambers 110 rigidize the flexible portion 28 is controlled by the movement of the trigger 40. When appropriate, the locking trigger 40 may be returned to the unlocked position to interrupt the supply of power to the coiled wire 114, and thus return the flexible portion 28 to a pliable configuration.

Figure 4:
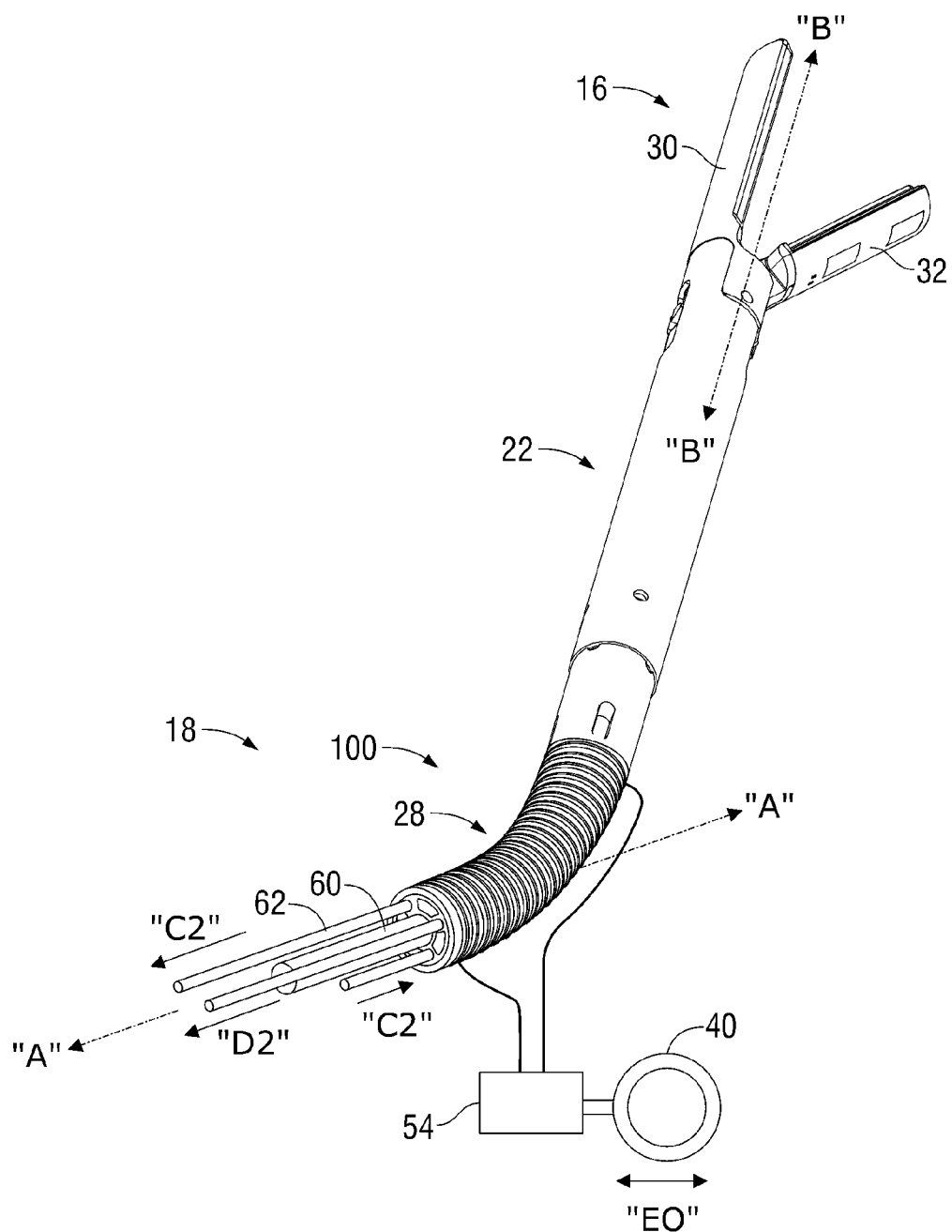
FIG. 4 is a partial, perspective view of the distal end of the instrument depicting the articulating portion of the instrument that is arranged in a curved configuration for maintaining the end effector in an articulated orientation.

Referring now to FIG. 4, when the locking mechanism 100 is in an unlocked configuration, and the flexible portion 28 is pliable, the distal portion 22 of the elongated shaft 18 may be moved to an articulated position. The surgeon may manipulate the articulation dials 42a, 42b (FIG. 1) to draw particular articulation cables 62 proximally while opposed articulation cables 62 are advanced distally as indicated by arrows "C2" and "D2." This opposed longitudinal motion in the articulation cables 62 induces the flexible portion 28 to bend, and allows the end effector 16 to be appropriately positioned and oriented relative to targeted tissue (not shown). The jaw members 30, 32 are moved to the open configuration to receive the tissue by manipulating pivoting handle 46 (FIG. 1) to move the drive tube 60.

The surgeon may move the locking trigger 40 to maintain the distal portion 22 of the elongated shaft 18 at the articulated position. By moving the locking trigger 40 to rigidize the flexible portion 28, the surgeon provides a stable platform for end effector 16 to be moved to the closed configuration about tissue. The jaw members 30, 32 are permitted to clamp the tissue with an appropriate closure force, and electrosurgical energy may be provided to treat the tissue without unintended motion of the end effector 16. Since the articulation cables 62 need not be engaged to maintain the articulated position of the distal portion 22, any movement or stretching of the articulation cables 62 will not be transmitted to the end effector 16. When the surgical procedure is complete, the surgeon may return the locking trigger 40 to the unlocked position to permit the flexible portion 28 to return to a pliable condition. The flexible portion 28 may then be returned to the aligned configuration depicted in FIG. 1 to facilitate withdrawal of the end effector 16 from the operative site through a cannula (not shown).

Referring now to FIG. 5, an alternate embodiment of a locking mechanism 200 is depicted with a flexible extrusion 202 arranged in a generally straight configuration. The extrusion 202 includes a central lumen 204, which permits passage of drive tube (not shown), electrical conduits, or other control mechanisms therethrough. The extrusion 202 defines a plurality of longitudinally spaced fluid chambers 210a, 210b therein. Each fluid chamber 210a, 210b is sealed with a plug 112 and filled with a ferrofluid "F." A proximal set of fluid chambers 210a is encircled by a coiled wire 214a that extends longitudinally to the same general extent as the proximal fluid chambers 210. A distal set of fluid chambers 210b is similarly encircled by a distal coil 214b that extends longitudinally to the same general extent as the distal fluid chambers 210b. Each of the coils 214a, 214b is independently coupled to a power source in the electrosurgical generator 54 such that an independent current may be induced to flow through each of the coils 214a and 214b.

In use, the viscosity of the ferrofluid "F" in each of the two sets of longitudinally spaced fluid chambers 210a, 210b may be independently controlled by controlling an electric current flowing through each of the respective coils 214a, 214b. Independent control of the viscosity of the ferrofluid "F" in each of the sets of fluid chambers 210a, 210b may, for example, facilitate the creation of compound curves in the extrusion 202. An "s-curve" may be created by sequentially creating oppositely directed bends in a proximal and distal portion of the extrusion 202. With the extrusion 202 in the straight configuration, a current may be induced to flow through only the distal coil 214b while no current flows through the proximal coil 214a. The proximal portion of the extrusion 202 will thus remain pliable while the distal portion will become more rigid. A surgeon may then induce bending of the proximal portion in the first direction while the distal portion remains generally straight. Thereafter, the surgeon may interrupt the current through the distal coil 214b while inducing a current to flow through the proximal coil 214a. The bend in the proximal portion of the extrusion 202 will be maintained due to the increased viscosity of the ferrofluid "F" in the proximal fluid chambers 210a, while the distal portion of the extrusion 202 becomes pliable. The surgeon may then impart a bend to the distal portion of the extrusion 202 in a direction opposite to the bend in the proximal portion of the extrusion 202.

The surgeon may employ a set of articulation cables 62 (FIG. 2) extending through articulation lumens (not shown) defined in the extrusion 202 to induce bending of the extrusion 202. Alternatively, another mechanism (not shown) may be provided with the instrument, or the surgeon may rely on external implements to induce the bending.

Referring now to FIG. 6, another alternate embodiment of a locking mechanism 200 is depicted with a flexible extrusion 302 arranged in a generally straight configuration. The extrusion 302 includes a central lumen 304, which permits passage of drive tube (not shown), electrical conduits, or other control mechanisms therethrough. The extrusion 302 defines a plurality of radially-spaced fluid chambers 310, similar to the radially spaced fluid chambers 110 described above with reference to FIG. 3. Each fluid chamber 310a, 310b is sealed with a pair of plugs 112 and filled with a ferrofluid "F." Each of the fluid chambers 310 is encircled by an independent coil 314a, 314b, which is coupled to an independent power source in the electrosurgical generator 54. The coils 314a, 314b provide independent control over the rigidity of the ferrofluid "F" in the fluid chambers 310.

The embodiments of the disclosure described above include a ferrofluid "F" disposed within fluid chambers 110, 210, 310. Other embodiments are envisioned in which other types of variable viscosity fluids are disposed in the fluid chambers 110, 210 and 310. For example, electro-rheological fluids (ER fluids) and magneto-rheological fluids (MR fluids) may also exhibit an appropriate change in rigidity in response to an applied electromagnetic field.

Although the foregoing disclosure has been described in some detail by way of illustration and example, for purposes of clarity or understanding, it will be obvious that certain changes and modifications may be practiced within the scope of the appended claims.

What is claimed is:

1. A surgical instrument, comprising:
   a shaft including at least one flexible portion;
   an end effector supported at a distal end of the shaft; and
   a locking mechanism operatively associated with the at least one flexible portion, the locking mechanism including:
      at least one fluid chamber defined within the flexible portion of the shaft;
      a variable viscosity fluid disposed within the at least one fluid chamber, the variable viscosity fluid configured to respond to an electromagnetic field such that the variable viscosity fluid exhibits an increased rigidity in the presence of the electromagnetic field and a reduced rigidity in the absence of the electromagnetic field; and
      at least one electrical coil arranged such that the electromagnetic field may be selectively induced about the at least one fluid chamber upon energizing the at least one electrical coil.

2. The surgical instrument according to claim 1, wherein the locking mechanism includes a plurality of electrical coils and wherein at least two of the electrical coils are independently energizable.

3. The surgical instrument according to claim 1, wherein the variable viscosity fluid includes a ferrofluid.

4. The surgical instrument according to claim 1, wherein the at least one fluid chamber includes a plurality of radially spaced fluid chambers defined within the flexible portion of the shaft.

5. The surgical instrument according to claim 1, wherein the at least one fluid chamber includes a plurality of longitudinally spaced fluid chambers defined in the flexible portion of the shaft.

6. The surgical instrument according to claim 1, wherein the end effector includes a pair of jaw members configured to grasp tissue therebetween.

7. The surgical instrument according to claim 1, wherein the end effector is configured to treat tissue with energy.

8. A surgical instrument, comprising:
   a shaft including at least one flexible portion;
   an end effector supported at a distal end of the shaft;
   at least one articulation cable extending at least partially through the shaft and operatively coupled to the shaft distally of the at least one flexible portion, the at least one articulation cable selectively manipulatable to induce an attendant motion of the at least one flexible portion of the shaft; and
   a locking mechanism operatively associated with the at least one flexible portion, the locking mechanism including:
      at least one fluid chamber defined within the flexible portion of the shaft;
      a variable viscosity fluid disposed within the at least one fluid chamber, the variable viscosity fluid configured to respond to an electromagnetic field such that the variable viscosity fluid exhibits an increased rigidity in the presence of the electromagnetic field and a reduced rigidity in the absence of the electromagnetic field.

9. The surgical instrument according to claim 8, further including an actuator operably coupled to the at least one articulation cable, the actuator configured to allow selective manipulation of the at least one articulation cable.

10. An articulating surgical instrument, comprising:
    a housing;
    an shaft extending distally from the housing, the shaft including at least one flexible portion;
    an end effector supported at a distal end of the shaft;
    at least one tensile member extending longitudinally through the shaft, the at least tensile member selectively movable to induce an attendant motion of the flexible portion of the shaft;
    a locking mechanism operatively associated with the flexible portion of the shaft and configured to selectively vary the rigidity of the flexible portion, the locking mechanism including:
       a variable viscosity fluid disposed within the flexible portion of the shaft, the variable viscosity fluid responsive to an electromagnetic field such that the variable viscosity fluid exhibits an increased rigidity in the presence of the electromagnetic field and a reduced rigidity in the absence of the electromagnetic field; and a field generator selectively operable to apply and remove the electromagnetic field.

11. The surgical instrument according to claim 10, wherein the at least one tensile member includes at least one pair of articulation cables selectively movable in opposed longitudinal directions to induce the attendant motion of the flexible portion of the shaft.

12. The surgical instrument according to claim 10, wherein the variable viscosity fluid includes a ferrofluid.

13. The surgical instrument according to claim 10, wherein the variable viscosity fluid is disposed within at least one fluid chamber defined within the flexible portion of the shaft.

14. The surgical instrument according to claim 13, wherein the at least one fluid chamber includes a plurality of radially spaced fluid chambers defined within the flexible portion of the shaft.

15. The surgical instrument according to claim 13, wherein the at least one fluid chamber includes a plurality of longitudinally spaced fluid chambers defined in the flexible portion of the shaft.

16. The surgical instrument according to claim 10, wherein the end effector includes a pair of jaw members configured to grasp tissue therebetween.

17. The surgical instrument according to claim 10, wherein the end effector is configured to treat tissue with energy.

18. An articulating surgical instrument, comprising:

a housing;

an shaft extending distally from the housing, the shaft including at least one flexible portion;

an end effector supported at a distal end of the shaft;

a locking mechanism operatively associated with the flexible portion of the shaft and configured to selectively vary the rigidity of the flexible portion, the locking mechanism including:

a variable viscosity fluid disposed within the flexible portion of the shaft, the variable viscosity fluid responsive to an electromagnetic field such that the variable viscosity fluid exhibits an increased rigidity in the presence of the electromagnetic field and a reduced rigidity in the absence of the electromagnetic field; and a field generator selectively operable to apply and remove the electromagnetic field, wherein the field generator includes a coiled conductor arranged about the flexible portion of the shaft, and wherein the coiled conductor is electrically coupled to a power source disposed within the housing.

* * * * *